United States Patent [19]

Sprecker

[11] Patent Number: 4,788,337
[45] Date of Patent: Nov. 29, 1988

[54] 2-ALKANOYL-2-(1-PENTEN-1-YL)CYCLOHEXANONES, PROCESS FOR PREPARING SAME, AND ORGANOLEPTIC USES THEREOF AND INTERMEDIATES USEFUL IN SAID PROCESS

[75] Inventor: Mark A. Sprecker, Sea Bright, N.J.

[73] Assignee: International Flavors & Fragrances Inc., New York, N.Y.

[21] Appl. No.: 149,657

[22] Filed: Jan. 28, 1988

[51] Int. Cl.$^4$ ............................................ C07C 49/647
[52] U.S. Cl. ...................................... 568/376; 512/23; 568/356
[58] Field of Search ........................................ 568/376

[56] References Cited

U.S. PATENT DOCUMENTS 3,431,305  3/1969  Thompson et al. ................. 568/376
3,578,715  5/1971  Corbier et al. ....................... 568/376
4,021,488  5/1977  Hall et al. ............................ 568/376

FOREIGN PATENT DOCUMENTS 2509415  9/1975  Fed. Rep. of Germany ...... 568/376

OTHER PUBLICATIONS

Fiaud et al., J. Organometallic Chem., vol. 154, pp. 175-178 (1978).
Fiaud, Chem. Abst., vol. 84, #43396k (1976).

Primary Examiner—James J. Reamer
Attorney, Agent, or Firm—Arthur L. Liberman

[57] ABSTRACT

Described are 2-alkanoyl-2-(1-penten-1-yl) cyclohexanones of my invention defined according to the structure:

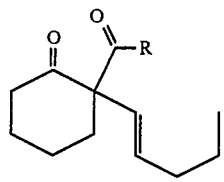

wherein R represents methyl or ethyl; a process for preparing same and organoleptic uses thereof in augmenting or enhancing the aroma of perfume compositions, colognes and perfumed articles including but not limited to solid or liquid anionic, cationic, nonionic or zwitterionic detergents, perfumed polymers, fabric softener compositions and fabric softener articles. Also described are intermediates useful in carrying out the process for producing such 2-alkanoyl-2-(1-penten-1-yl) cyclohexanones of my invention defined according to the structure:

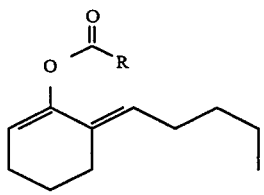

wherein R represents methyl or ethyl.

3 Claims, 6 Drawing Sheets

GLC PROFILE FOR EXAMPLE I.
CRUDE

GLC PROFILE FOR EXAMPLE I.
FIRST DISTILLATION

GLC PROFILE FOR EXAMPLE II.
CRUDE

FIG. 5 NMR SPECTRUM FOR EXAMPLE II

2-ALKANOYL-2-(1-PENTEN-1-YL)CYCLOHEXANONES, PROCESS FOR PREPARING SAME, AND ORGANOLEPTIC USES THEREOF AND INTERMEDIATES USEFUL IN SAID PROCESS

BACKGROUND OF THE INVENTION

The invention relates to the 2-alkanoyl-2-(1-penten-1-yl)cyclohexanones of my invention defined according to the structure:

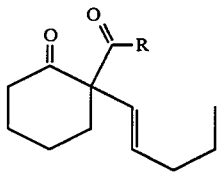

wherein R represents methyl or ethyl and uses thereof in augmenting or enhancing the aroma of perfume compositions, colognes and perfumed articles.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Jasmine, herbaceous, fatty, smoky, sweaty, and animalic aromas with myrrh and wintergreen topnotes (particularly those aromas that have a high degree of substantivity and a high strength) are desirable in many types of perfume compositions, colognes and perfumed articles.

The compounds having the structure:

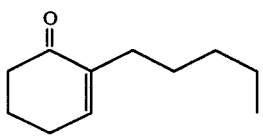

is known to be useful in perfumery. A need exists in the perfume industry to produce this compound having the structure:

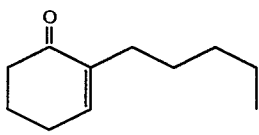

and an attempt was made to produce it using the compound having the structure:

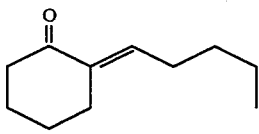

by means of rearrangement of the double bond into the ring. Such an attempt however gave rise to unexpected, unobvious and advantageous results yielding the compound having the structure:

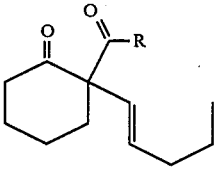

as a result of the attempt to react the compound having the structure:

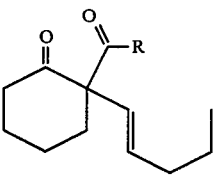

with acetic or propionic anhydride and then heating the resulting reaction product.

Indeed, nothing in the prior art discloses the compounds defined according to the structure:

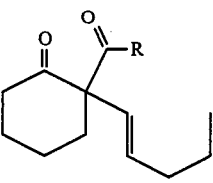

wherein R represents methyl or ethyl or the intermediates useful in producing such compounds defined according to the structure:

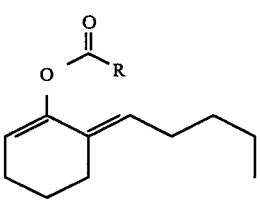

wherein R represents methyl or ethyl.

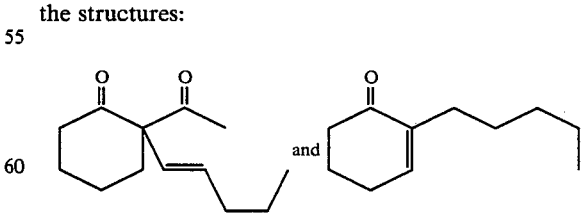

as well as cumene. (Conditions: SE-30 column programmed at 180° C. isothermal).

Figure 2:
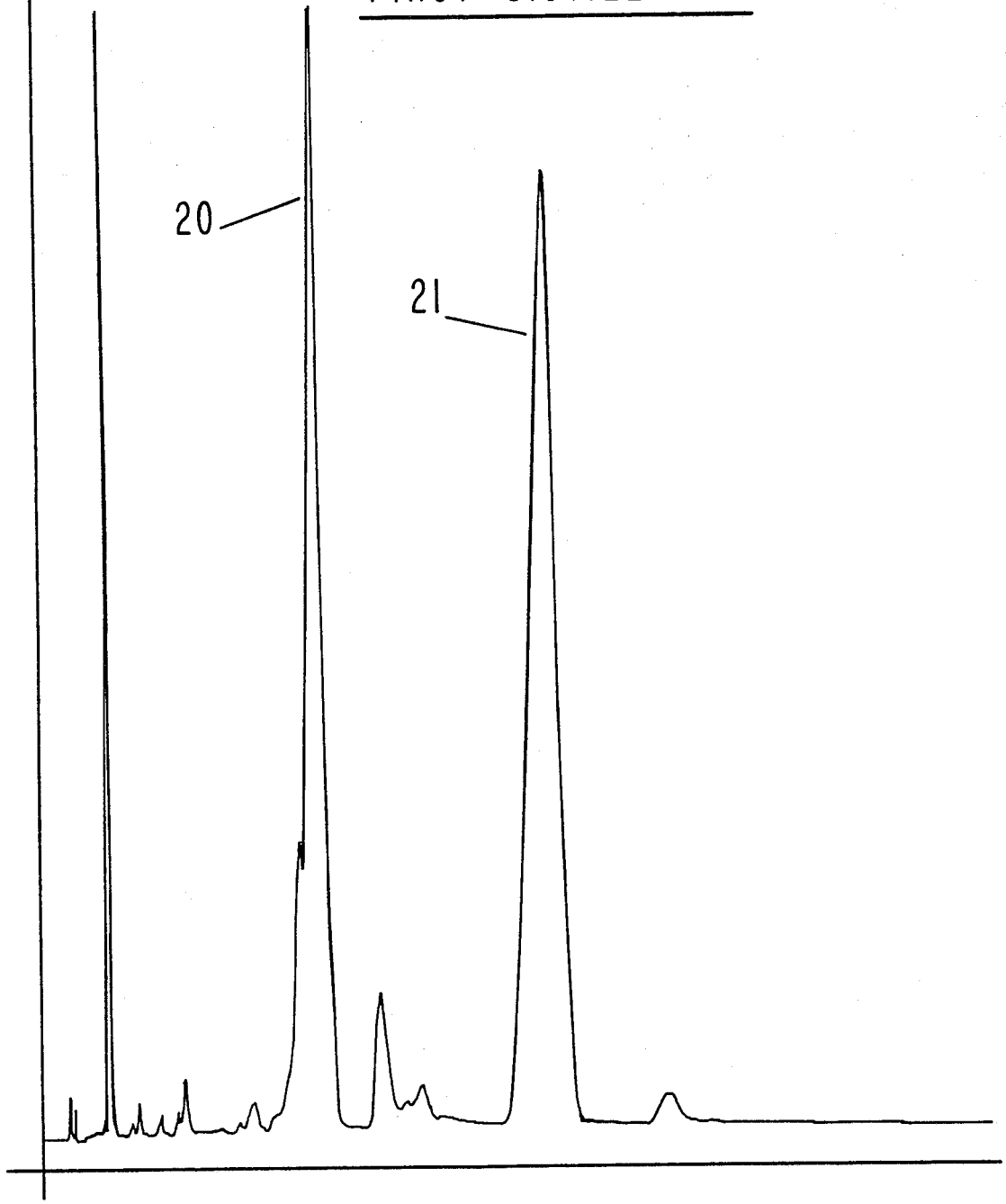

FIG. 2 is the GLC profile for the first distillation product of the reaction product of Example I containing the compounds having the structures:

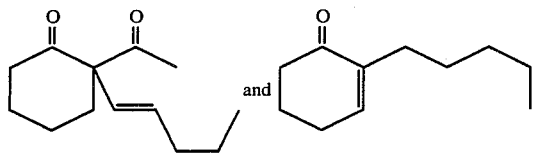

(Conditions: SE-30 column programmed at 180° C. isothermal).

Figure 3:
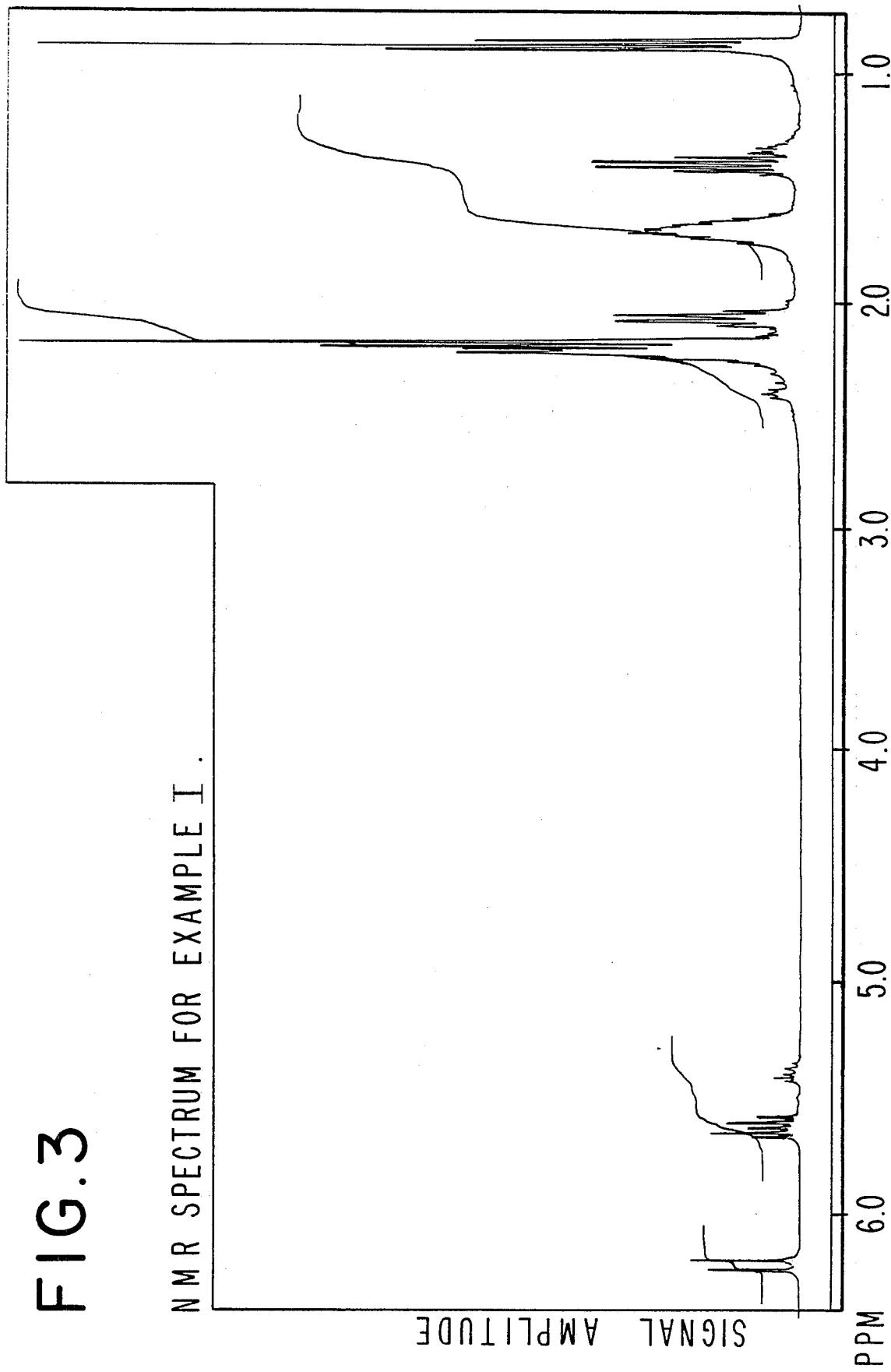

FIG. 3 is the NMR spectrum for the compound having the structure:

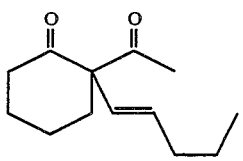

produced according to Example I.

Figure 4:
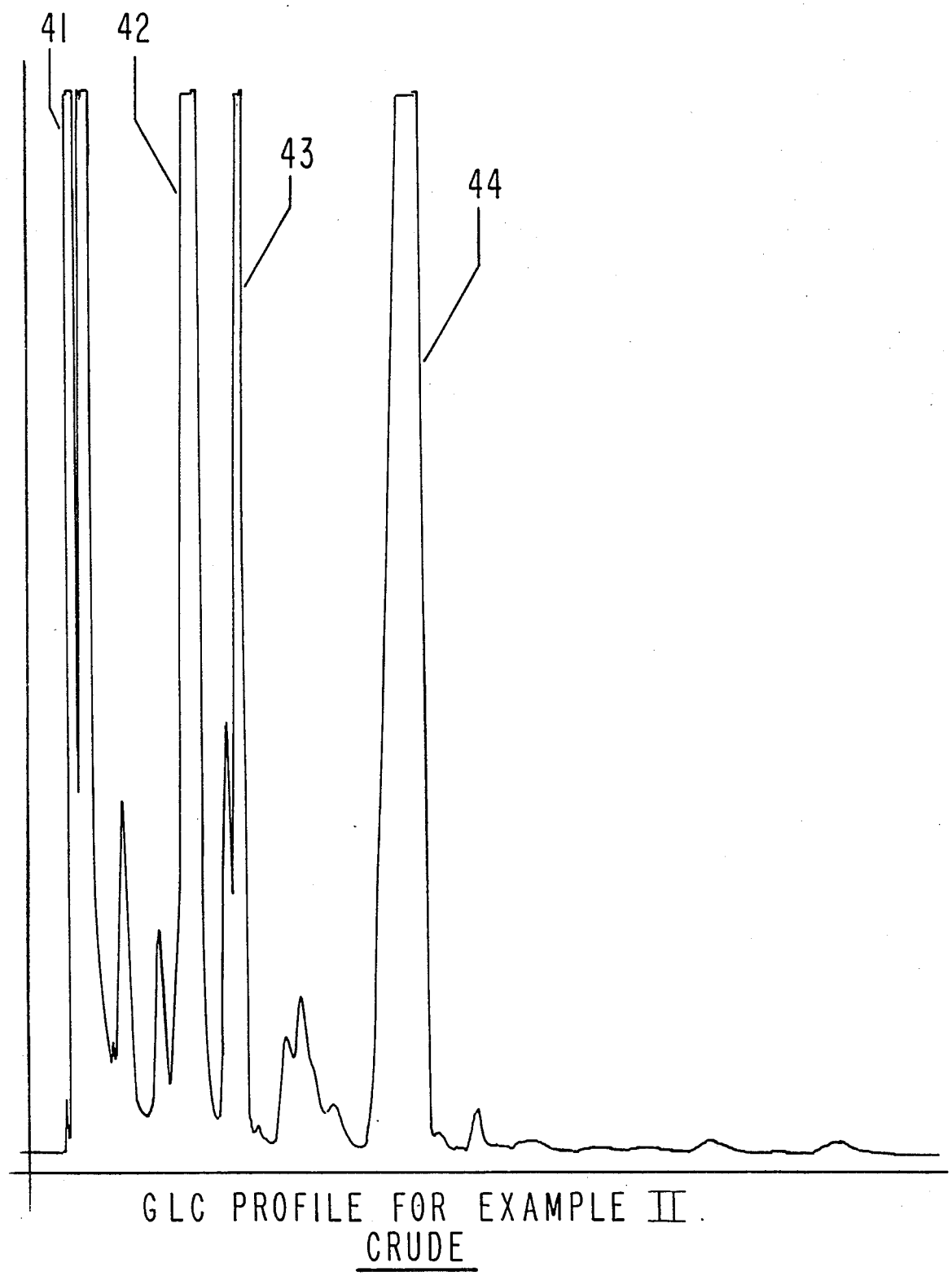

FIG. 4 is the GLC profile for the crude reaction product of Example II containing the compounds having the structures:

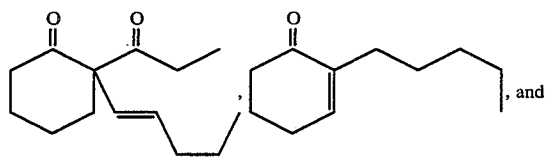

as well as cumene and propionic acid.

Figure 5:
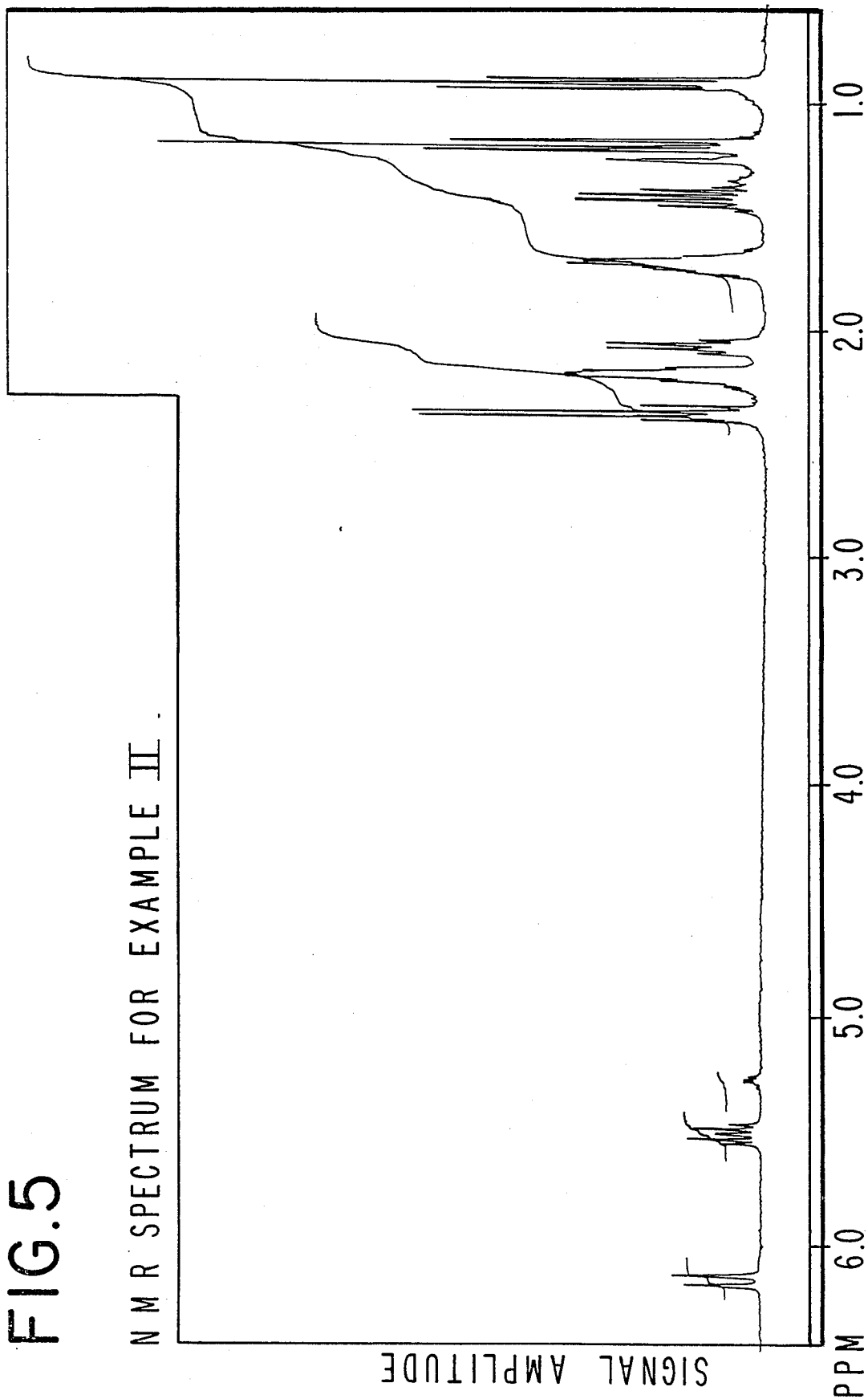

FIG. 5 is the NMR spectrum for the compound having the structure:

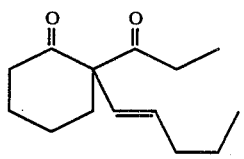

produced according to Example II.

Figure 6:
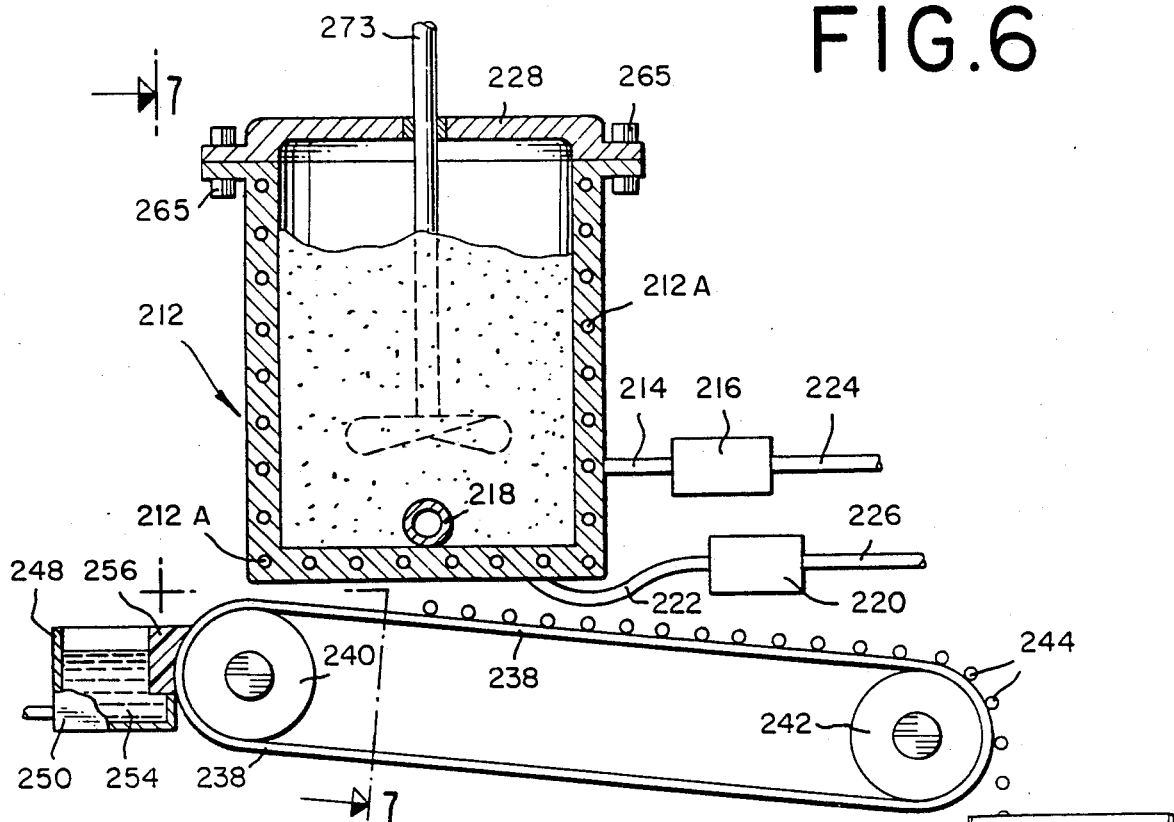

FIG. 6 represents a cut-away side elevation view of apparatus used in forming perfumed polymers containing at least one of the 2-alkanoyl-2-(1-pentene-1-yl)cyclohexanones of my invention defined according to the structure:

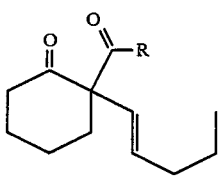

wherein R represents methyl or ethyl.

Figure 7:
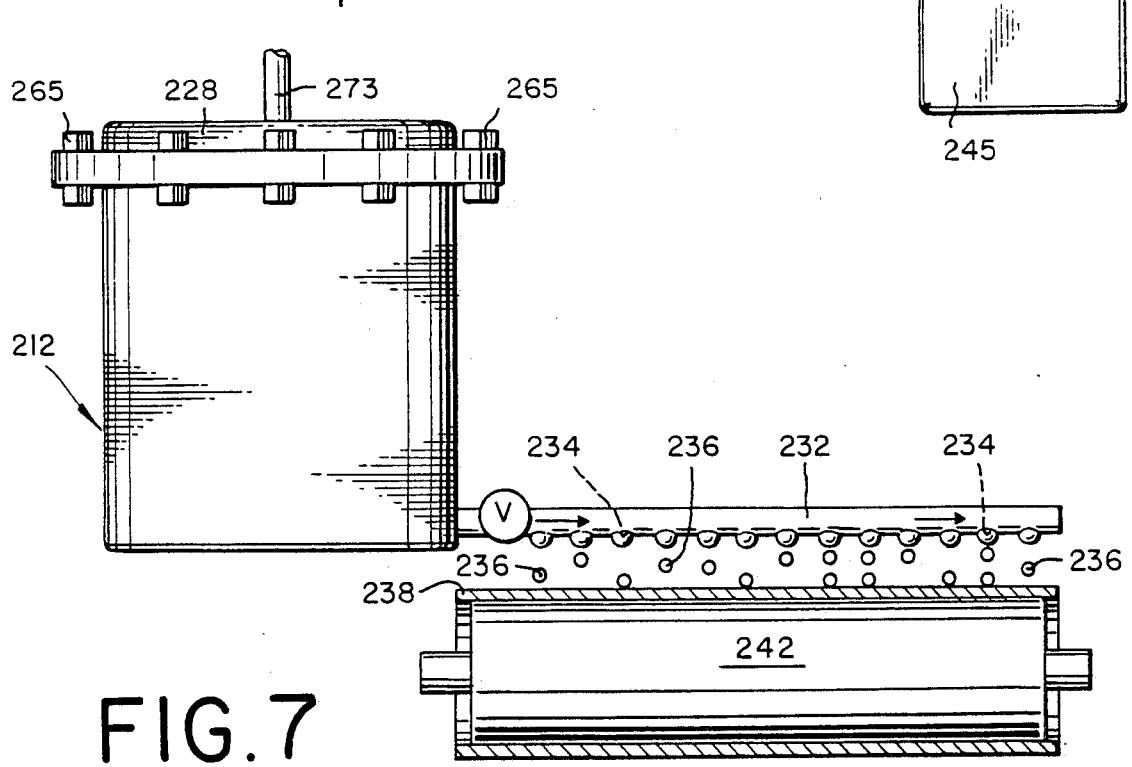

FIG. 7 is a front view of the apparatus of FIG. 6 looking in the direction of the arrows.

DETAILED DESCRIPTION OF THE DRAWINGS

Figure 1:
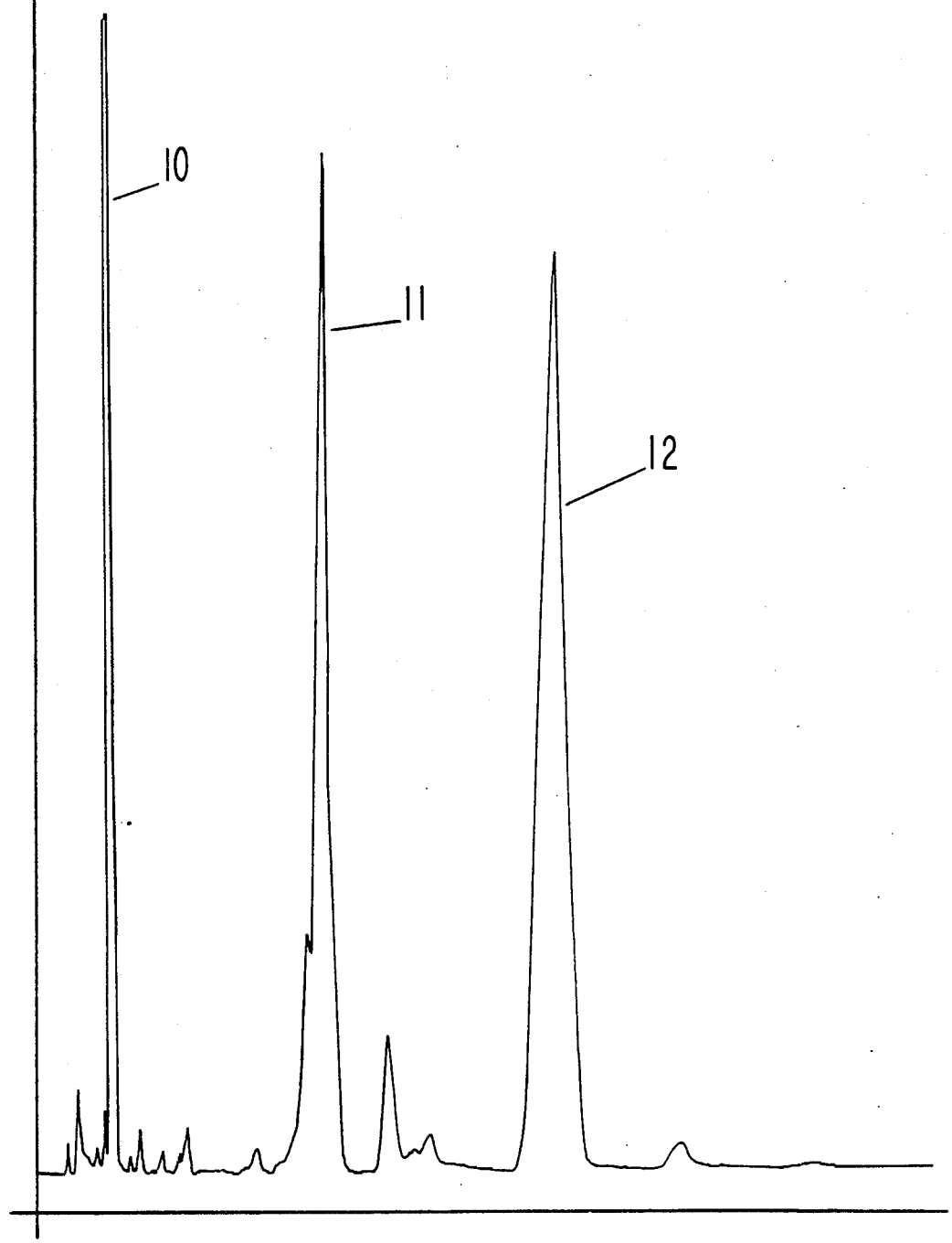
FIG. 1 is the GLC profile for the crude reaction product of Example I containing the compounds having the structures.

FIG. 1 is the GLC profile for the crude reaction product of Example I (Conditions: SE-30 column programmed at 180° C. isothermal). The peak indicated by reference numeral 10 is the peak for cumene. The peak indicated by reference numeral 11 is the peak for the compound having the structure:

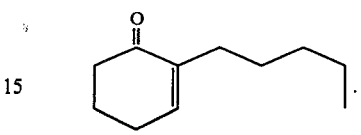

The peak indicated by reference numeral 12 is the peak for the compound having the structure:

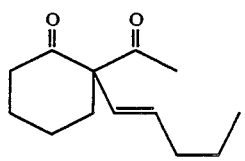

FIG. 2 is the GLC profile for the first distillation product of the reaction product of Example I (Conditions: SE-30 column programmed at 180° C. isothermal). The peak indicated by reference numeral 20 is the peak for the compound having the structure:

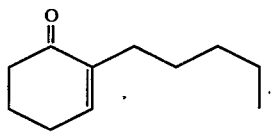

The peak indicated by reference numeral 21 is the peak for the compound having the structure:

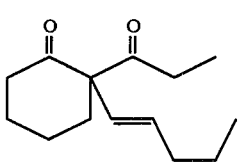

FIG. 4 is the GLC profile for the crude reaction product of Example II (Conditions: SE-30 column programmed at 180° C. isothermal). The peak indicated by reference numeral 41 is the peak for cumene and propionic acid. The peak indicated by reference numeral 42 is the peak for the compound having the structure:

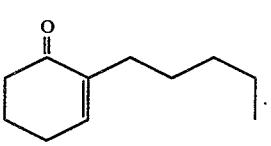

The peak indicated by reference numeral 43 is the peak for the compound having the structure:

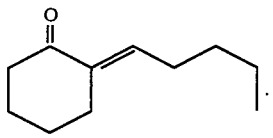

The peak indicated by reference numeral 44 is the peak for the compound having the structure:

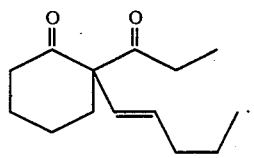

Referring to FIGS. 6 and 7, there is provided a process for forming scented polymer pellets (wherein the polymer may be thermoplastic polymers such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 6 and 7, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance defined according to the structure:

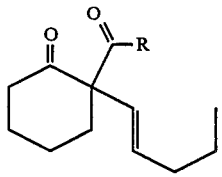

wherein R represents methyl or ethyl is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 250°–260° C. in the case of low density polyethylene. The bottom portion of the container 212 is heated by means of heating coils 212A regulated through the control 220 connected thereto through a connecting wire 222 to maintain the lower portion of the container 212 within a temperature range of 250°–270° C.

Thus, the polymer or mixture of polymers added to the container 212 is heated from 10–12 hours, whereafter the perfume composition or perfume material consisting of compounds defined according to the structure:

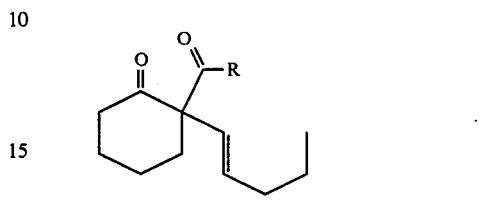

wherein R represents methyl or ethyl is quickly added to the melt. Generally, about 10–45 percent by weight of the resulting mixture of the perfumery substance is added to the polymer.

After the perfume material is added to the container 212 the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer intimately admixed with the perfume substance defined according to the structure:

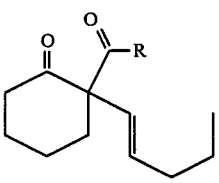

wherein R represents methyl or ethyl or mixture containing said perfume substance will continuously drop through the orifices 234 downwardly from the conduit 232. During this time, the temperature of the polymer intimately admixed with the perfumery substance in the container 212 is accurately controlled so that a temperature in the range of from about 250°–260° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume materials defined according to the structure:

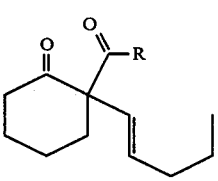

wherein R represents methyl or ethyl through the orifices 234 at a range which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

THE INVENTION

It has now been discovered that novel solid and liquid perfume compositions, colognes and perfumed articles (e.g., solid or liquid anionic, cationic, nonionic or zwitterionic detergents, fabric softeners, drier-added fabric softener articles, hair preparations and perfumed polymers) having intense and substantive jasmine, herbaceous, fatty, smoky, sweaty and animalic aromas with myrrh and wintergreen topnotes may be provided by the utilization of one or more of the 2-alkanoyl-2-(1-penten-1-yl)cyclohexanones of my invention having the structure:

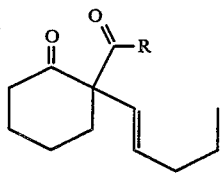

wherein R represents methyl or ethyl in perfume compositions, perfumed articles and colognes.

The 2-alkanoyl-2-(1-penten-1-yl)cyclohexanones of my invention may be produced by means of reacting the compound having the structure:

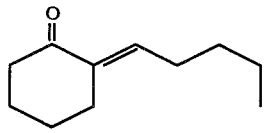

with propionic anhydride or acetic anhydride or a mixed acetic-propionic anhydride defined according to the structure:

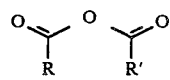

wherein R and R' are the same or different methyl or ethyl in order to form enol esters defined according to the structure:

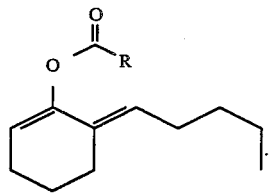

The enol esters are then heated in the presence of a protonic acid catalyst or a Lewis acid catalyst to form a mixture of the two compounds; the compound having the structure:

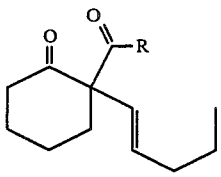

and compounds defined according to the structure:

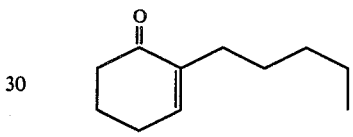

wherein R represents methyl or ethyl.

The crude reaction product is then separated into its components, for example, by means of fractional distillation.

More specifically, the reaction sequence taking place may be shown, thusly:

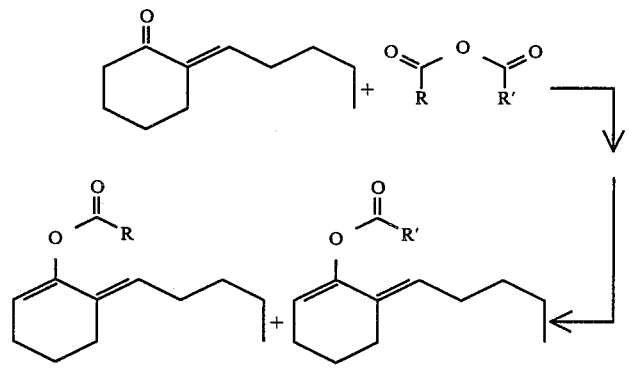

and

-continued

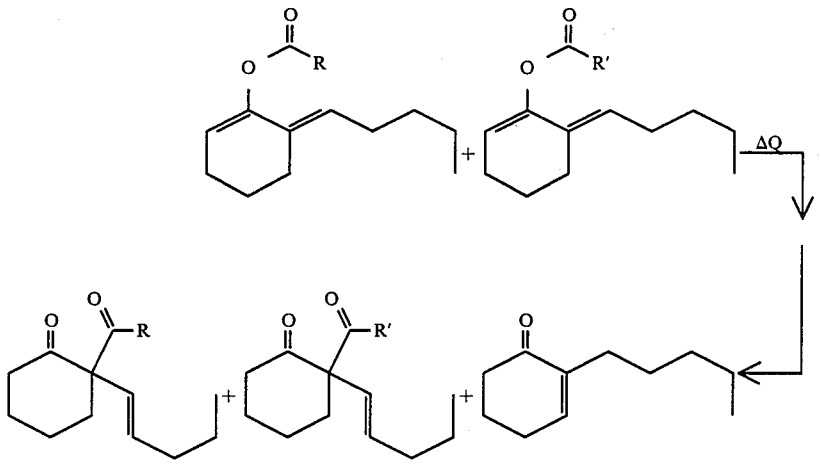

wherein R and R' represent the same or different methyl or ethyl.

With reference to the reaction between the propionic or acetic anhydride with the compound having the structure:

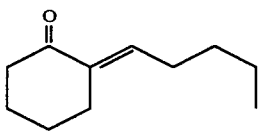

in order to form the enol esters defined according to the structure:

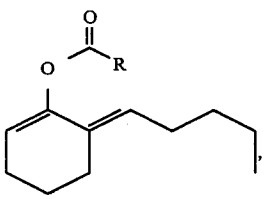

the reaction is carried out at temperatures in the range of from about 50° C. up to about 180° C., with temperatures in the range of 130°–150° C. being preferred. The reaction is also carried out in a solvent such as a hydrocarbon solvent or a chlorocarbon solvent, for example, cumene, a solvent which can be utilized at the reflux temperature of the reaction mass and which can be utilized at the temperature at which the reaction can proceed.

The mole ratio of acetic or propionic anhydride:compound having the structure:

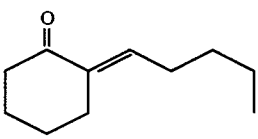

may vary from about 1:2 down to about 2:1 with mole ratios of about 1:1 being preferred.

With respect to the conversion of the enol ester to the product mixture containing the compounds having the structures:

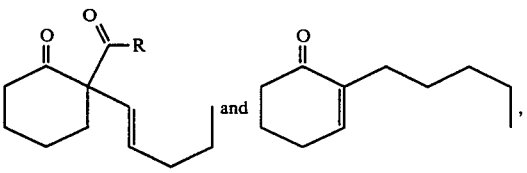

the reaction preferably takes place in the presence of an acid, a protonic acid such as paratoluene sulphonic acid, sulfuric acid or phosphoric acid or a Lewis acid such as boron trifluoride, boron trifluoride etherate, stannous chloride, zinc chloride or aluminum chloride or diethyl aluminum chloride. The concentration of the acid in the reaction mass may vary from about 1 up to about 5% by weight of the reaction mass.

At the end of the reaction, the reaction products are separated as by fractional distillation; and the resulting reaction products may then be used for their organoleptic properties.

Examples of the 2-alkanoyl-2-(1-penten-1-yl)cyclohexanones useful in the practice of my invention and their organoleptic properties are as follows:

TABLE I

| Structure of The Compound | Organoleptic Characteristic |
|---|---|
| | A smoky, powerful, sweaty animalic aroma with myrrh and wintergreen topnotes. |
| | A jasmine, herbaceous fatty aroma. |

The 2-alkanoyl-2-(1-penten-1-yl)cyclohexanones of my invention and one or more auxiliary perfume ingredients, including, for example, hydrocarbons, alcohols, ketones other than the ketones of my invention, aldehydes, nitriles, esters, lactones or cyclic esters, synthetic essential oils and natural essential oils, may be admixed so that the combined odors of the individual components produce a pleasant and desired fragrance, particularly and preferably jasmine, herbaceous, fatty, smoky, sweaty and animalic aromas with myrrh and wintergreen topnotes.

Such perfume compositions usually contain (a) the main note or the "bouquet" or the foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh-smelling materials.

In perfume compositions, it is the individual components which contribute to their particular olfactory characteristics, however the overall sensory effect of the perfume composition will be at least the sum total of the effects of each of the ingredients. Thus, one or more of the 2-alkanoyl-2-(1-penten-1-yl)cyclohexanones of my invention can be used to alter, modify or enhance the aroma characteristics of a perfume composition, for example, by utilizing or moderating the olfactory reaction contributed by another ingredient in the composition.

The amount of 2-alkanoyl-2-(1-penten-1-yl)cyclohexanones of my invention which will be effective in perfume compositions as well as perfumed articles and colognes depends on many factors, including the other ingredients, their amounts and the effect which are desired. It has been found that perfume compositions containing as little as 0.01% of the 2-alkanoyl-2-(1-penten-1-yl)cyclohexanones of my invention or even less (e.g., 0.005%) can be used to impart a jasmine, herbaceous, fatty, smoky, sweaty animalic aroma with myrrh and wintergreen topnotes to soaps, detergents (including anionic, cationic, nonionic or zwitterionic solid or liquid detergents) cosmetics, fabric softener articles, fabric whiteners, optical brighteners and perfumed polymers. The amount employed can range up to 70% of the fragrance compositions and will depend on consideration of cost, nature of the end product, the effect desired on the finished product and the particular fragrance sought.

The 2-alkanoyl-2-(1-penten-1-yl)cyclohexanones of my invention are useful (taken alone or together with other ingredients in perfume compositions) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders such as talcs, dusting powders, face powders and the like. As little as 0.005% of the 2-alkanoyl-2-(1-penten-1-yl)cyclohexanones of my invention (in the ultimate perfumed article) will suffice to impart a jasmine, herbaceous, fatty, smoky, sweaty and animalic aromas with myrrh and wintergreen topnotes to various types of perfumed articles. Generally, no more than 3% of the 2-alkanoyl-2-(1-penten-1-yl)cyclohexanones of my invention based on the ultimate end product (perfumed article) is required. Thus, the range in perfumed articles of the use of the 2-alkanoyl-2-(1-penten-1-yl)cyclohexanones of my invention are from about 0.005% up to about 3% by weight of the ultimate perfumed article.

In addition, the perfume composition or fragrance composition of my invention can contain a fragrance, or carrier for the 2-alkanoyl-2-(1-penten-1-yl)cyclohexanones of my invention. The vehicle can be a liquid such as a non-toxic alcohol, e.g., ethyl alcohol, a non-toxic glycol, e.g., propylene glycol or the like. The carrier can also be an absorbent such as a gum (e.g., gum arabic, xanthan gum or guar gum), or components for encapsulating the composition (such as gelatin by means of coacervation or such as a urea formaldehyde polymer when forming a polymer wall around a liquid perfume center).

My invention also relates to the utilization of controlled release technology for the controlled release of perfumes into gaseous environments from polymers such as mixtures of epsilon polycaprolactone polymers and polyethylene which poly epsilon caprolactone polymers are defined according to at least one of the structures:

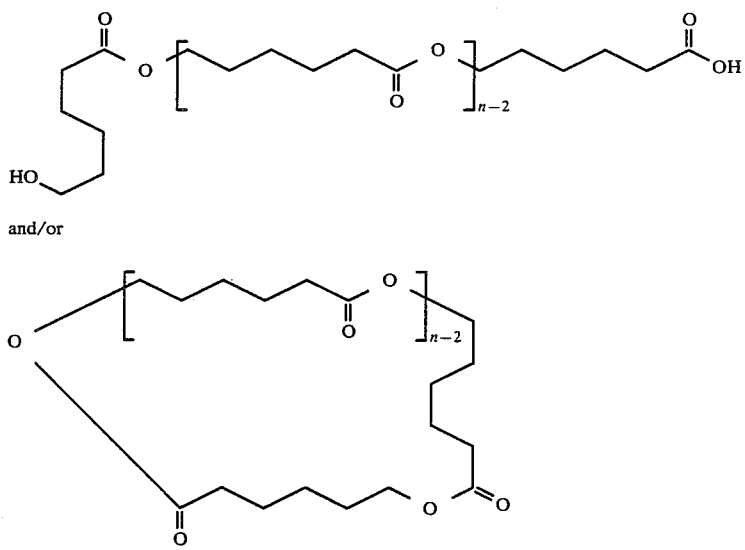

and/or wherein "n" is from about 50 up to about 1,200 with the proviso that the average "n" in the system varies from about 150 up to about 700 according to the mathematical statement:

$$[700 \geq n \geq 150]$$

with the term n̄ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$\frac{dM}{dt} = k_1 e^{-k_2 t}$$

wherein $k_1$ and $k_2$ are constants. According to Kydonieus, "Controlled Release Technologies: Methods, Theory, and Applications" (cited, supra), the amount of functional fluid released system which are describable as physically dispersed nonerodible polymeric or elastomeric matrices is proportional to time as long as the concentration of functional fluid present (dispersed and dissolved) is higher than the solubility of the agent in the matrix. Thus, such dispersed systems are similar to the dissolved systems except that instead of a decreased release rate after 60% of the functional fluid has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the genus defined according to the structure:

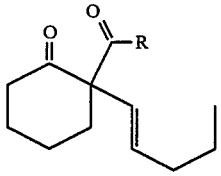

wherein R represents methyl or ethyl.

The polyepsilon caprolactone polymers useful in practicing my invention is more specifically described in the brochure of the Union Carbide Corporation, 270 Park Avenue, New York, N.Y. 10017, entitled "NEW POLYCAPROLACTONE THERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of my invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with my invention against discoloration are dihydroxybenzenes such hydroquinone or compounds having the formula:

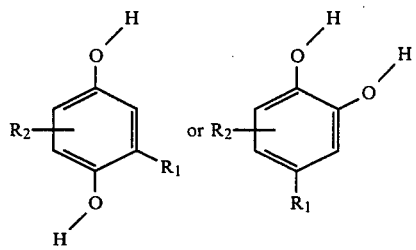

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method of incorporating the 2-alkanoyl-2-(1-penten-1-yl)cyclohexanones of my invention defined according to the structure:

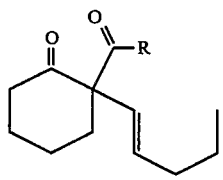

wherein R represents methyl or ethyl or perfume compositions containing same into the polymers may be according to the technique, for example, U.S. Pat. No. 3,505,432 issued on Apr. 7, 1970 (the specification for which is incorporated by reference herein), or U.S. Pat. No. 4,247,498 issued on Jan. 27, 1981, the disclosure of which is incorporated by reference herein.

Thus, for example, a first amount of liquid polyethylene-polyepsilon caprolactone polymer mixture (50:50) is mixed with a perfume material such as the compound having the structure:

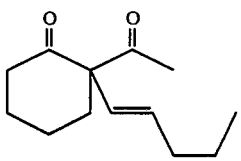

Drops are formed from the mixture and the drops are solidified. The solidified drops are then melted, if desired, with a second amount of unscented low density polyethylene, for example, polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of my invention the imparting of scent is effected in two stages. In a first stage, a 50:50 (weight:weight) polyepsilon caprolactone, e.g., PCL-7009:polyethylene in molten form is admixed with a high percentage of scent imparting material having the structure:

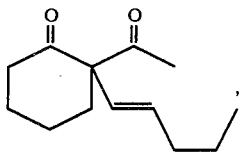

for example, and the mixture is solidified in the form of pellets or beads. These pellets or beads thus contain a high percentage of material having the structure:

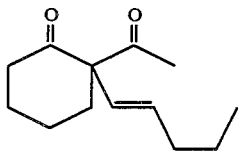

(e.g., up to 40% by weight of the entire mixture) and may be used as "master pellets" which thereafter, in a second stage, if desired, may be admixed and liquified with additional polymers such as additional polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention the aroma containing material, for example, that having the structure:

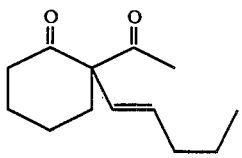

is added to the polymer in a large closed container or drum which is maintained under controlled temperature conditions while the polymer in a melted condition is mixed with the perfume material under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by the perfume is permitted to drip through the orifices onto a continuously moving, cooled conveyor upon which the polymer containing the perfume solidifies into small size pellets with the perfume imprisoned therein. The apparatus useful in conjunction with this process advantageously includes a conveyor of a material which will not adhere to the polymer which contains the perfume. In order that the droplets form into uniform pellets or beads, the conveyor is continuously washed with a liquid such as water to maintain the surface relatively cool. The pellets are delivered by the conveyor into a container and packaged for shipment.

The following examples serve to illustrate processes for producing the 2-alkanoyl-2-(1-penten-1-yl)cyclohexanones of my invention (Examples I and II) as well as processes for utilizing the 2-alkanoyl-2-(1-penten-1-yl)cyclohexanones of my invention for their organoleptic utilities (Examples III, et seq).

All parts and percentages given herein are by weight unless otherwise specified.

EXAMPLE I

PREPARATION OF 2-ACETYL-2-(1-PENTEN-1-YL)CYCLOHEXANONE

Reactions:

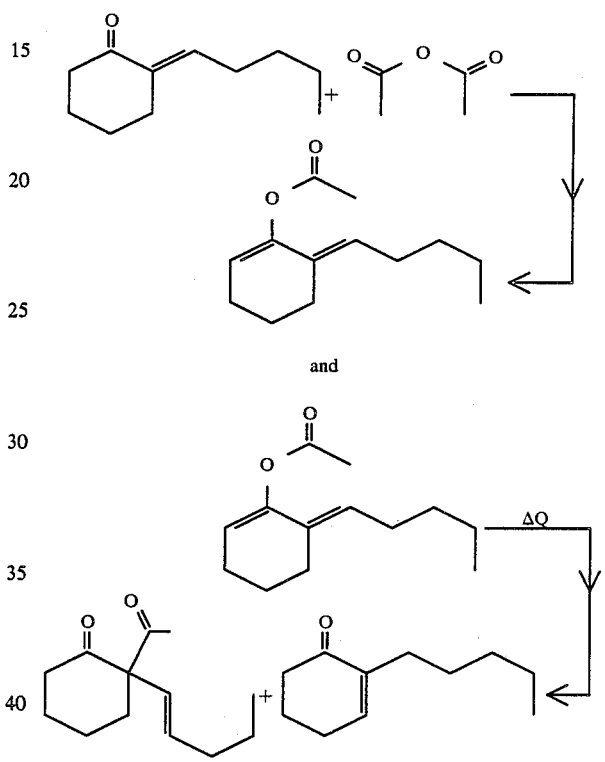

Into a 5 liter reaction flask equipped with stirrer, thermometer, reflux condenser and heating mantle are placed 1175 grams of pentylidene cyclohexanone having the structure:

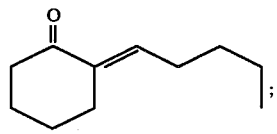

17.68 grams of paratoluene sulphonic acid; 323 grams of cumene and 705 grams of acetic anhydride.

The resulting mixture is heated to reflux and refluxed for a period of eight hours at a temperature in the range of 130°–140° C.

At the end of the eight hour period, the reaction mass is cooled to 80° C. and 1 liter of water is added.

The reaction mass is then washed with one 400 ml portion of water followed by one 400 ml portion of saturated sodium chloride.

The reaction mass is then distilled on a 3″ stone packed column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 35/36 | 60/72 | 4.0/4.0 | 152.4 |
| 2 | 90 | 102 | 4.0 | 132.4 |
| 3 | 100 | 110 | 4.0 | 147.8 |
| 4 | 113 | 130 | 5.5 | 448.2 |
| 5 | 127 | 157 | 10.0 | 352.2 |
| 6 | 129 | 200 | 14.0 | 50.0. |

Fractions 3–6 are bulked and redistilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 38/80 | 110/110 | 3.8/3.8 | 9:1 |
| 2 | 86 | 110 | 3.8 | 9:1 |
| 3 | 80 | 108 | 3.8 | |
| 4 | 88 | 108 | 4.0 | 9:1 |
| 5 | 88 | 109 | 4.0 | 9:1 |
| 6 | 89 | 110 | 4.0 | 9:1 |
| 7 | 90 | 112 | 4.0 | 9:1 |
| 8 | 94 | 114 | 4.0 | 9:1 |
| 9 | 102 | 115 | 4.0 | 9:1 |
| 10 | 107 | 116 | 4.0 | 9:1 |
| 11 | 108 | 116 | 4.0 | 9:1 |
| 12 | 110 | 116 | 4.0 | 9:1 |
| 13 | 110 | 116 | 4.0 | 4:1 |
| 14 | 110 | 116 | 4.0 | 4:1 |
| 15 | 110 | 116 | 4.0 | 4:1 |
| 16 | 110 | 118 | 4.0 | 1:1 |
| 17 | 110 | 131 | 4.0 | 1:1 |
| 18 | 112 | 120 | 4.0 | |
| 19 | 112 | 210 | 4.0 | 1:1 |
| 20 | 112 | 210 | 4.0 | 1:1. |

Fractions 2–9 are bulked and IR, NMR and mass spectral analysis yield the information that these fractions are the compound having the structure:

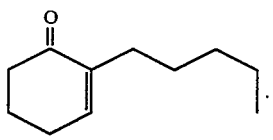

Fractions 11–19 are bulked and NMR, IR and mass spectral analysis indicate that these compounds are the substances having the structure:

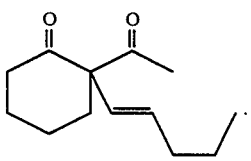

FIG. 1 is the GLC profile for the crude reaction product (Conditions: SE-30 column programmed at 180° C. isothermal). The peak indicated by reference numeral 10 is the peak for cumene the solvent for the reaction. The peak indicated by reference numeral 11 is the peak for the reaction product having the structure:

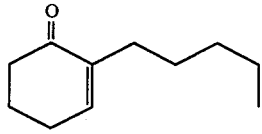

The peak indicated by reference numeral 12 is the peak for the reaction product having the structure:

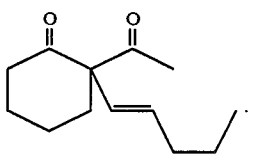

FIG. 2 is the GLC profile for the first distillation (bulked fractions 3–6). The peak indicated by reference numeral 20 is the peak for the reaction product having the structure:

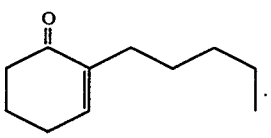

The peak indicated by reference numeral 21 is the peak for the reaction product having the structure:

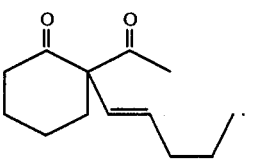

FIG. 3 is the NMR spectrum for the compound having the structure:

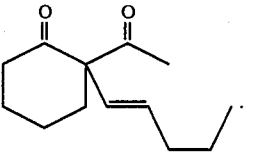

The resulting product has an intense and highly substantive smoky, sweaty and animalic aroma with myrrh and wintergreen topnotes.

EXAMPLE II

PREPARATION OF 2-PROPIONYL-2-(1-PENTEN-1-YL)-CYCLOHEXANONE

Reactions:

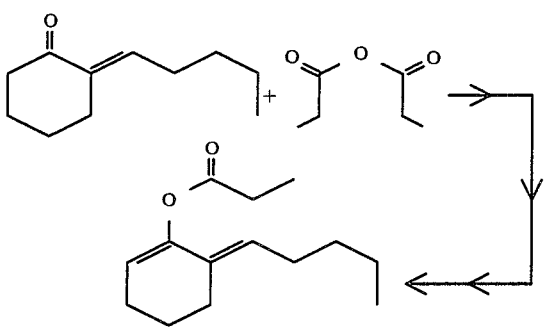

and

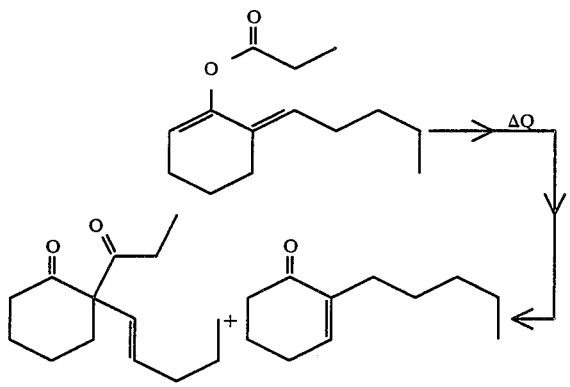

Into a 1 liter reaction flask equipped with stirrer, thermometer, reflux condenser and heating mantle are placed 200 grams of pentylidene cyclohexanone having the structure:

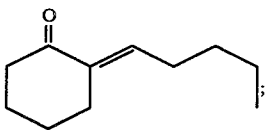

7.5 grams of paratoluene sulphonic acid; 55 grams of cumene and 156 grams of propionic anhydride.

The resulting mixture is heated to reflux and refluxed at a temperature in the range of 130°-140° C. for a period of six hours.

The reaction mass is then cooled to 90° C. and 200 ml water is added thereto. The organic phase is separated from the aqueous phase and the organic phase is washed with 200 ml salt solution followed by 5 ml of 50% sodium hydroxide.

The reaction mass is then distilled on a 3" splash column yielding the following fractions:

| Fraction No. | Vapor Temp. (°C.) | Liquid Temp. (°C.) | Vacuum mm/Hg. Pressure |
|---|---|---|---|
| 1 | 35/36 | 50/55 | 4.0/4.0 |
| 2 | 41 | 67 | 5.0 |
| 3 | 51 | 98 | 5.0 |
| 4 | 85 | 115 | 4.5 |
| 5 | 90 | 123 | 4.0 |
| 6 | 125 | 185 | 4.0 |
| 7 | 147 | 205 | 4.0. |
| 8 | 147 | 210 | |

Fractions 5 and 6 are bulked. These fractions according to NMR, IR and mass spectral analysis have the structure:

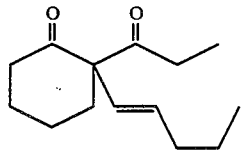

Fractions 5 and 6 are redistilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 57/75 | 104/104 | 2.8/2.8 | 9:1/9:1 | 3.5 |
| 2 | 80 | 105 | 2.8 | 9:1 | 3.6 |
| 3 | 80 | 107 | 2.8 | 9:1 | 10.3 |
| 4 | 80 | 110 | 2.8 | 9:1 | 9.5 |
| 5 | 80 | 114 | 2.8 | 9:1 | 8.1 |
| 6 | 80 | 118 | 2.8 | 9:1 | 9.2 |
| 7 | 80 | 125 | 2.8 | 9:1 | 7.2 |
| 8 | 80 | 143 | 2.8 | 9:1 | 4.6 |
| 9 | 88 | 157 | 2.8 | | 4.5 |
| 10 | 75 | 180 | 2.8 | 9:1 | 3.4 |

The resulting product having the structure:

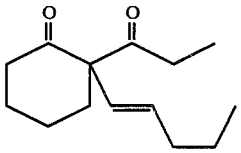

has a very intense jasmine, herbaceous and fatty aroma.

FIG. 4 is the GLC profile for the crude reaction product prior to distillation.

The peak indicated by reference numeral 41 is the peak for cumene, the solvent for the reaction and propionic acid a reaction product. The peak indicated by reference numeral 42 is the peak for the compound having the structure:

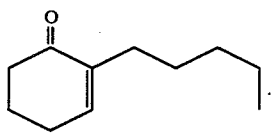

The peak indicated by reference numeral 43 is the peak for the reactant (unreacted) having the structure:

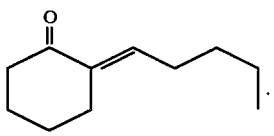

The peak indicated by reference numeral 44 is the peak for the reaction product having the structure:

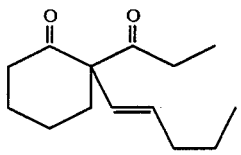

FIG. 5 is the NMR spectrum for the compound having the structure:

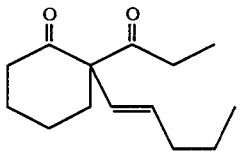

EXAMPLE III

The following jasmine, musk and jasmine/musk formulae are prepared:

| Ingredients | Parts by Weight | | |
|---|---|---|---|
| | III(A) | III(B) | III(C) |
| Jasmine Oil | 0.0 | 10.0 | 10.0 |
| Geranium Bourbon | 20.0 | 20.0 | 20.0 |
| Rosemary Oil Spanish | 10.0 | 10.0 | 10.0 |
| Lavender Oil Barreme | 10.0 | 10.0 | 10.0 |
| Thyme Oil White | 10.0 | 10.0 | 10.0 |
| Amyl Cinnamic Aldehyde | 10.0 | 10.0 | 10.0 |
| Sauge Sclaree French | 5.0 | 5.0 | 5.0 |
| Sandalwood Oil | 5.0 | 5.0 | 5.0 |
| Galbanum Oil | 5.0 | 5.0 | 5.0 |
| Patchouli Oil Light | 5.0 | 5.0 | 5.0 |
| Cedarwood Oil Light | 15.0 | 15.0 | 15.0 |
| The compound having the structure: produced according to Example I. | 5.0 | 0.0 | 5.0 |
| The compound having the structure: produced according to Example II. | 0.0 | 5.0 | 5.0 |
| Cyclohexadecanone | 10.0 | 0.0 | 10.0 |
| Musk Xylol | 8.0 | 0.0 | 8.0 |

When the composition of matter prepared according to Example I is added into this formula an interesting smoky, sweaty, animalic undertone with myrrh and wintergreen topnotes is added to the musk formulation of Example III(A).

The overall composition can be described from an organoleptic standpoint as "musky and floral aroma with intense smoky, sweaty and animalic undertones and myrrh and wintergreen topnotes.

With reference to the formulation of Example III(B), the compound having the structure:

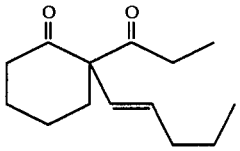

imparts a powerful jasmine, herbaceous and fatty undertone to this jasmine/floral formulation. The overall formulation of Example III(B) can be described as "jasmine and herbaceous with a fatty undertone".

When the mixture of compounds having the structures:

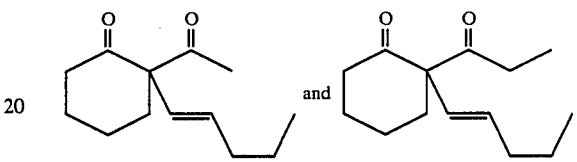

prepared respectively according to Examples I and II is added to the formulation of Example III(C), intense jasmine, herbaceous, fatty, smoky, sweaty and animalic undertones with myrrh and wintergreen topnotes are imparted to this musky/jasmine formulation. The overall organoleptic description of this formulation is "a jasmine and musky aroma with herbaceous, fatty, smoky, sweaty and animalic undertones and myrrh and wintergreen topnotes".

EXAMPLE IV

A stable lotion is prepared with the following formulation:

| Ingredients | Parts by Weight |
|---|---|
| Poly(N,N—dimethyl-3,5-dimethylene piperidinium chloride) (Merquat 100, Merck & Co., U.S.A., average molecular weight 50,000–100,000, viscosity in 40% aqueous solution, 10,000 cps | 1.0 |
| Cocoamidopropyl dimethyl glycine (betaine) | 5.7 |
| Myristyl dimethylamine oxide | 12.0 |
| Stearic monoethanolamide opacifier | 2.0 |
| Perfume material as indicated in Table II (below) giving rise to the aroma profiles as indicated in Table II (below) | 0.5 |
| Water, colour, salts, U.V. absorber | q.s. to 100 |

Two or three bottle capfuls of the above lotion held under the tap releasing the water into the bathtub yields a copiously foamed bubble bath with no visible precipitation, flocculation, or "bathtub ring" even using hard water. Bathing in this bath is found to have a cleansing and pleasing emollient effect on the skin as described above.

When, after immersion in this bath, the body is soaped, rinsed and dried, an even better, more long-lasting emollient, moisturizing effect on the skin is observed. The foam or bubbles are substantially unaffected by the soaping step, and no precipitate, flocculate or "bathtub ring", or any bothersome film or coating on the bathtub surface is found.

The aroma produced is as set forth in Table II, below:

TABLE II

| Product | Aroma Profile |
| --- | --- |
| The compound having the structure: (structure with two C=O groups on cyclohexane ring with ethyl and allyl substituents) | A smoky, sweaty, animalic aroma having a high substantivity and strength with myrrh and wintergreen topnotes. |
| The compound having the structure: (structure with two C=O groups on cyclohexane ring with ethyl and allyl substituents) | A jasmine, herbaceous and fatty aroma having high strength and high substantivity. |
| Perfume composition prepared according to Example (III)A. | A musky and floral aroma with intense smoky, sweaty and animalic undertones and myrrh and wintergreen topnotes. |
| Perfume composition prepared according to Example III(B). | Jasmine and herbaceous aroma with fatty undertone. |
| Perfume composition prepared according to to Example III(C). | Jasmine and musky aroma with herbaceous, fatty, smoky, sweaty and animalic undertones and myrrh and wintergreen topnotes. |

EXAMPLE V

SHAMPOO

The following shampoo is prepared containing the following ingredients:

| Ingredients | Parts by Weight |
| --- | --- |
| Tridecyloxy polyethoxy ethanol of ten ethoxy groups | 17.3 |
| Polyoxyethylene (20) sorbitan monolaurate | 7.5 |
| Myristyl dimethylamine oxide (30% active) | 25.0 |
| $C_{10}$-$C_{20}$ fatty acyl mono-ethanolamide (cocomonoethanolamide) | 2.5 |
| Polyacrylamide of molecular weight of about 1,500,000 | 0.2 |
| Hydrogen peroxide (30% aqueous solution) | 0.5 |
| Perfume ingredient as indicated at Table II of Example IV giveing rise to aroma profile as indicated in Table II of Example IV | 1.0 |
| Deionized water (3 micromhos/cm conductivity) | 46.0 |

A shampoo of the above composition is made in the following manner. First, the tridecyloxy polyethoxy ethanol is added to a clean mixing tank, with the agitator on, and the amine oxide, polyoxyethylene sorbitan monolaurate and cocomonoethanolamine are added sequentially, with continued agitation. The mix is then heated to 68° C., until the cocomonoethanolamide is melted and/or dissolved. The hydrogen peroxide solution is then admixed with the mentioned nonionics and mixing is continued for about half an hour, in which the peroxide destroys any free amines or other harmful impurities that may be present. The mix is then cooled to 38° C.

In a separate mixer the polyacrylamide is gradually added to the formula weight of deionized water, with the mixer on. Addition is effected carefully and slowly (the polyacrylamide is sprinkled in) to avoid the production of "fish eyes" in the mix. After dissolving of the polyacrylamide the solution thereof is added to the first mixing tank with agitation and is blended with the nonionics, such mixings being at room temperature. Subsequently the perfume as indicated in Table II of Example IV, supra, giving rise to the aroma profile as set forth in Table II of Example IV, supra, is admixed with the balance of the composition and mixing is continued for another half hour.

The product made is an excellent shampoo of satisfactory viscosity and aroma, foaming power, foam stability, low conductivity and good shampooing effects. The viscosity is about 1,000 centipoises at 20° C. and the conductivity, using the Hach Conductivity Meter, is 750 micromhos/cm. The foaming power is 250 ml and the foam stability is 22 seconds, by the test method previously described. In comparison, a commercial shampoo based on triethanolamine lauryl sulphate detergent has a conductivity of about 22,000 micromhos/cm, a viscosity of about 1,500 centipoises, a foaming power of about 380 ml and a foam stability of 60 seconds.

In panel evaluations of the experimental shampoo compared to a different commercial product, in actual shampooing, the experimental formula was adjudged significantly better in being less drying, producing a softer feel for the wet hair, leaving the wet hair easier to comb, being less prone to accumulate static charges (less flyaway) and having a foam of better appearance and feel. Additionally, the experimental product was judged better in almost all hair effect properties, with the control only being about equal to it in curl retention. In properties other than those mentioned the experimental product was better in rinsability, the control was better in foam build-up rate and the foams were about equal in volume and stability.

In the shampooing described herein and in subsequent Examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel-dried and dried further with an automatic hair dryer.

EXAMPLE VI

FABRIC FRESHENER COMPOSITION

A fabric freshener composition is prepared as follows:

| Ingredients | Parts by Weight |
| --- | --- |
| Sodium bicarbonate | 3.0 |
| "Kyro" EOB (Trademark) | 1.0 |
| Perfume ingredient as set forth in Table II of Example IV giving rise to an aroma as set forth in Table II of Example IV | 0.05 |
| Water | 0.05 |

The composition of this Example is prepared by simply mixing the ingredients.

The above described composition is applied to lightly soiled and wrinkled fabric as droplets (ca. 5.0 mm avg. size) using a trigger action sprayer having a nozzle which is adjustable to provide composition droplets in the desired range. The composition is applied at a rate of about 1 gram of composition to about 10 grams of fabric.

The fabric is then placed in an automatic dryer and dried with tumbling action, at a temperature of 60°-80° C. for a period of 15 minutes. The fabric is rendered free of wrinkles and static, and has a fresh appearance and pleasant odor profile as set forth in Table II of Example IV, supra. The sodium bicarbonate is not visible on the refreshed fabric.

EXAMPLE VII

PERFUMED LIQUID DETERGENT

Concentrated liquid detergents (lysine salts of n-dodecyl benzene sulfonic acid as more specifically described in U.S. Pat. No. 3,948,818 issued on Apr. 6, 1976, (the specification for which is incorporated by reference herein) with aromas as indicated in Table II of Example IV, supra, are prepared containing 0.10%, 0.15%, 0.20%, 0.25%, 0.30%, 0.40%, 0.50% and 0.80% of the perfume ingredient as set forth in Table II of Example IV, supra. The detergents are prepared by adding and homogeneously mixing the appropriate quantity of perfume ingredient as set forth in Table II of Example IV, supra. The detergents all possess aromas as set forth in Table II of Example IV, supra, with the intensity of each increasing with greater concentrations of the perfume ingredient as stated in Table II of Example IV, supra.

EXAMPLE VIII

PREPARATION OF A COLOGNE AND HANDKERCHIEF PERFUME

The perfume ingredient as set forth in Table II of Example IV, supra, are incorporated into colognes at concentrations of 2.0%, 2.5%, 3.0%, 3.5%, 4.0%, 5.0% and 6.0% in 75%, 80%, 85%, 90% and 95% aqueous ethanol solutions. Distinct and definite aromas as set forth in Table II of Example IV, supra, are imparted to the colognes. The perfume ingredients as indicated in Table II of Example IV, supra, are also added to handkerchief perfumes at concentrations of 15%, 20%, 25%, 30% and 35% (in 75%, 80%, 85%, 90% and 95% aqueous ethanol solutions) and aroma profiles as set forth in Table II of Example IV, supra, are imparted to the handkerchief perfume.

EXAMPLE IX

PREPARATION OF A DETERGENT COMPOSITION

A total of 100 grams of detergent powder (a low phosphate content detergent composition which contains 12% by weight phosphate builder, 8% hardness mineral ion insensitive detergent, 0.9% by weight maleic anhydride-vinyl compound co-polymer and 2% alkylene oxide condensation product prepared according to Example IV at column IX, U.S. Pat. No. 4,000,080 issued on Dec. 28, 1976, (the specification for which is incorporated by reference herein) is intimately admixed with 0.15 grams of one of the perfume materials of Table II of Example IV, supra, until a substantially homogeneous composition is obtained. The composition has an aroma as set forth in Table II of Example IV, supra.

EXAMPLE X

Each of the fragranced materials of Table II of Example IV, supra, are added to a 50:50 weight:weight mixture of low density polyethylene:polyepsilon caprolactone PCL-700 forming pellets with scents as set forth in Table II of Example IV, supra:

75 Pounds of a mixture of PCL-700 polyepsilon caprolactone (manufactured by the Union Carbide Corporation of New York, N.Y. having a melting point of about 180°-190° F.): Low density polyethylene are heated to about 250° C. in a container of the kind illustrated in FIGS. 6 and 7. 25 Pounds of each of the fragrance materials as set forth in Table II of Example IV, is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table II of Example IV, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example IV, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table II of Example IV, supra.

What is claimed is:

1. An 2-alkanoyl-2-(1-penten-1-yl)cyclohexanone defined according to the structure:

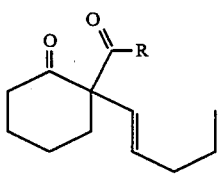

wherein R represents methyl or ethyl.

2. The 2-alkanoyl-2-(1-penten-1-yl)cyclohexanones of claim 1 wherein R represents methyl, having the structure:

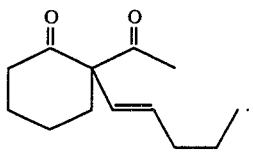
3. The 2-alkanoyl-2-(1-penten-1-yl)cyclohexanones of claim 1 wherein R is ethyl having the structure:
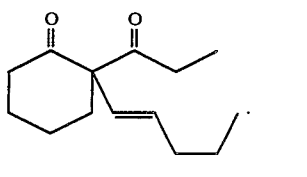
* * * * *